United States Patent [19]

Soong

[11] Patent Number: 4,570,478
[45] Date of Patent: Feb. 18, 1986

[54] CONCENTRIC-CYLINDER RHEOMETER
[75] Inventor: David S. Soong, Albany, Calif.
[73] Assignee: The Regents of The University of California, Berkeley, Calif.
[21] Appl. No.: 721,153
[22] Filed: Apr. 8, 1985
[51] Int. Cl.$^4$ ............................................. G01N 11/10
[52] U.S. Cl. ......................................................... 73/60
[58] Field of Search ................................ 73/60, 58, 54
[56] References Cited

U.S. PATENT DOCUMENTS

| | | | |
|---|---|---|---|
| 2,156,407 | 5/1939 | Stewart | 73/58 |
| 3,803,903 | 4/1974 | Lin | 73/59 |
| 3,864,961 | 2/1975 | Cessna, Jr. | 73/54 |
| 3,935,729 | 2/1976 | McCarthy | 73/60 |
| 4,062,225 | 12/1977 | Murphy, Jr. et al. | 73/60 |
| 4,299,118 | 11/1981 | Gau et al. | 73/59 |
| 4,352,287 | 10/1982 | Orth et al. | 73/60 |

FOREIGN PATENT DOCUMENTS

| | | | |
|---|---|---|---|
| 931199 | 8/1955 | Fed. Rep. of Germany | 73/60 |
| 2754074 | 6/1979 | Fed. Rep. of Germany | 73/60 |
| 18742 | 2/1981 | Japan | 73/60 |
| 655933 | 4/1979 | U.S.S.R. | 73/60 |

OTHER PUBLICATIONS

Myers, A. W., et al., *A Modified Pochettino Viscometer for the Measurement of the Viscoelastic Properties of High Polymer Melts*, Jn. Trans. Soc. of Rheo. 12:1, p. 183-193, 1968.

McCarthy, R. V., *An Improved Rheometer Design Used to Measure Viscoelastic Properties of Polymer Melts*, Jn. Rheo. 22(6), p. 623-641, 1968.

Primary Examiner—Stewart J. Levy
Assistant Examiner—Joseph W. Roskos
Attorney, Agent, or Firm—Fliesler, Dubb, Meyer & Lovejoy

[57] ABSTRACT

A rheometer (10) is disclosed which includes a central cylinder (14) surrounded by a tube (24) having a cylindrical bore (26), the bore (26) being slightly larger than the cylinder (14). A loading cup (44) has an interior cylindrical opening (50) larger than the bore (26) which extends from a first end portion (46) thereof toward a second end portion (48) thereof. The first end portion (46) of the cup (44) is detachably attachable to the tube (24) with the cylindrical opening generally coaxial with the bore (26) of the tube (24). An axial moving structure (34) serves for controllably axially moving the tube (24) relative to the cylinder (14). A measuring device (84) serves for measuring the instantaneous force exerted on the cylinder (14) as the tube (24) moves axially.

6 Claims, 3 Drawing Figures

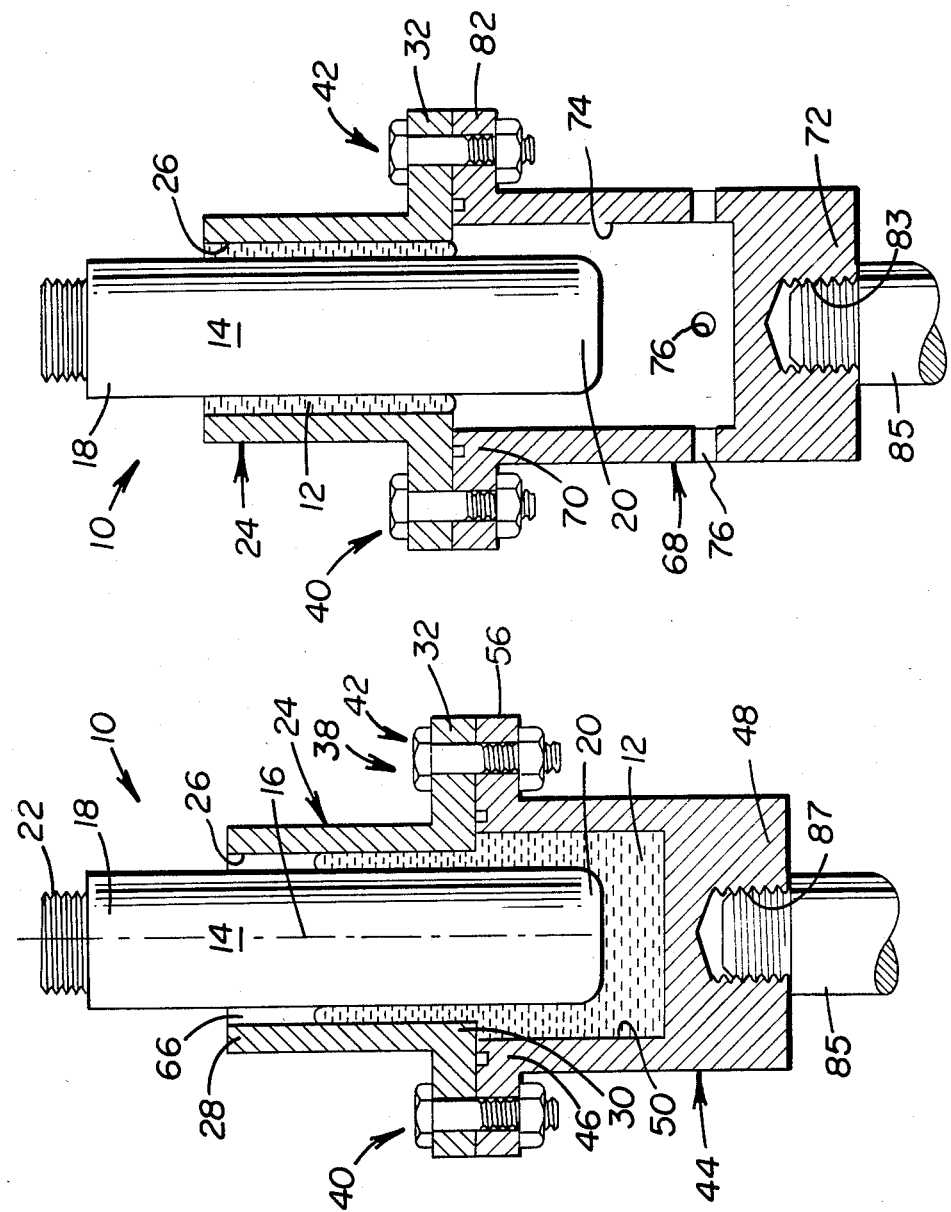

CONCENTRIC-CYLINDER RHEOMETER

TECHNICAL FIELD

The invention relates to a rheometer for measuring viscosity and very fast time dependent or transient viscosity phenomena in fluids. More particularly, the invention relates to a concentric-cylinder rheometer.

BACKGROUND ART

Various rheometric devices are available to measure viscosity and transient flow phenomena. In a number of such devices, a fluid is positioned between two generally parallel members, one of the members is moved parallel to the other member, and the resulting force exerted upon the member which is not moved is measured. In this manner the viscometric properties of the entrapped fluid can be measured.

In recent years there has been a constant proliferation of new rheometrical techniques and commercially manufactured test devices. Various geometrical configurations have been developed for studying viscoelastic fluids, such as sliding plate and cylinder, capillary, slit, couette, cone and plate, fiber spinning, sheet inflation and other complex flows. Paralleling these advances in experimental capabilities has been the development of network and reptation theories to describe the rheological properties of polymer melts and concentrated solutions. Particular emphasis has been placed on the behavior of such systems in transient flows. Theoretical development has in turn created further stringent demands on instrumentation. This trend of increasing sophistication of modeling and experimentation has been stimulated by the constant attempt to elucidate the complex dynamics of viscoelastic fluids in order to improve the design and control of polymer processing operations.

Prior art designs for making the appropriate shear measurements have generally not been adequate to provide the reproducible shear measurements which are required to keep up with the development in theory.

DISCLOSURE OF INVENTION

The present invention is directed to solving one or more of the problems as set forth above.

In accordance with the present invention, a rheometer is provided which comprises a central cylinder having an axis, a first and a second end. A tube having a cylindrical bore which is slightly larger than the cylinder is positioned about the cylinder and coaxial therewith, with first and second open ends of the tube aligned toward the first and second ends of the cylinder. A loading cup is provided having first and second end portions and on interior cylindrical opening larger than the bore of the tube and extending from the first end portion toward the second end portion with the first end portion of the cup being detachably attachable to the second open end of the tube with the cylindrical opening generally coaxial with the bore.

Axial moving means serve for controllably axially moving the tube relative to the cylinder, and measuring means serve for measuring the instantaneous force exerted on the cylinder as the tube moves axially.

A rheometer in accordance with the present invention is quite easy to load using the loading cup mentioned above. The rheometer is particularly useful for the measurement of fast transient and steady-state responses of viscoelastic fluids in simple shear. Shearing is accomplished via coaxial displacement of the outer tube while the inner cylinder is held stationary. Matching pairs of central cylinder and tube with precise dimensions, and thus well-defined annular spacings, are commercially available. Stress signals generated are generally free of noise. Instrumental compliance, material inertia and mechanical lag in both input and output components of the system are minimal. Reproducible shear stress data are obtainable for various complicated flow programs.

BRIEF DESCRIPTION OF THE DRAWINGS

The invention will be better understood by reference to the figures of the drawings wherein:

FIG. 1 illustrates, in side section, a rheometer in accordance with an embodiment of the present invention during loading of a fluid therein for testing;

FIG. 2 illustrates the rheometer, as in FIG. 1, set up for testing; and

BEST MODE FOR CARRYING OUT THE INVENTION

Figure 3:
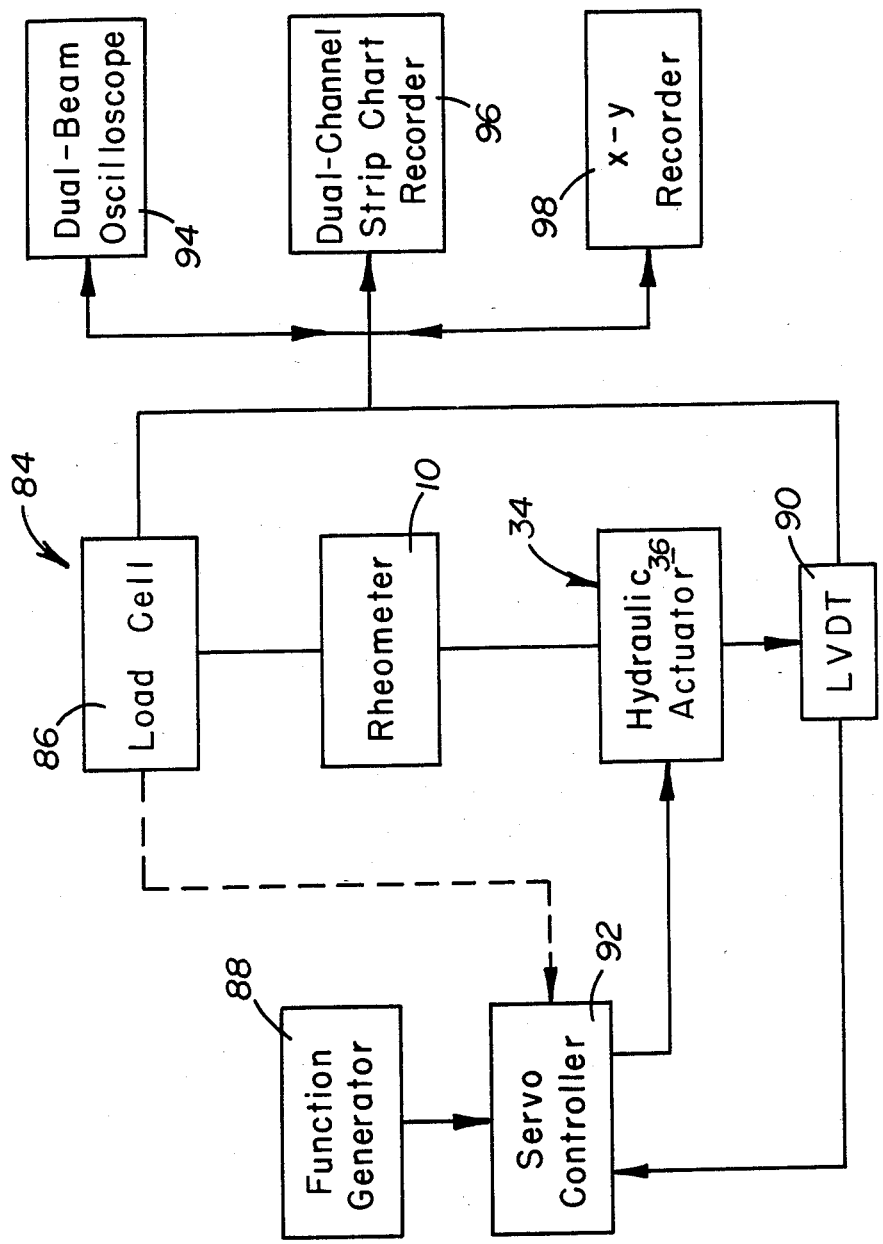
FIG. 3 illustrates, schematically, control and measuring apparatus useful in conjunction with a rheometer as illustrated in FIGS. 1 and 2.

A rheometer 10 in accordance with the present invention is illustrated in FIGS. 1 and 2. FIG. 1 shows the rheometer 10 being loaded with a viscous fluid 12. FIG. 2 shows the rheometer 10 in its testing or measuring mode.

The rheometer 10 includes a central cylinder 14 having an axis 16, a first end 18 and a second end 20. The first end 18 normally includes a threaded portion 22 which serves a purpose which will be explained below.

A tube 24 is provided which has a central bore 26 which is slightly larger than the cylinder 14. The bore 26 is positioned about the cylinder 14 and coaxial therewith. The tube 24 has a first open end 28 and a second open end 30 which are aligned toward, respectively, the first end 18 and the second end 20 of the cylinder 14. The second open end 30 of the tube 24 generally includes an outwardly extending mounting flange 32 which is attached to axial moving means 34 (FIG. 3) which serve for controllably axially moving the tube 24 relative to the cylinder 14. The axial moving means 34 can comprise, for example, a hydraulic motor 36 as illustrated schematically in FIG. 3 and fastening means 38 for connecting the hydraulic motor 36 to the mounting flange 32. The particular fastening means 38 illustrated comprises several pairs of nuts and bolts combinations 40 and 42 which are located about and appropriately fastened to the mounting flange 32 along with other members which will be described below.

FIG. 1 illustrates the rheometer 10 in the loading position. In that situation a loading cup 44 is connected to the tube 24. The loading cup 44 has a first end portion 46 and a second end portion 48. It also has an interior cylindrical opening 50 which is larger than the bore 26 and extends from the first end portion 46 toward the second end portion 48. The first end portion 46 of the cup 44 is detachably attachable to the second open end 30 of the tube 24 with the cylindrical opening 50 generally coaxial with the bore 26. The attachment generally is via the nut and bolt combinations 40 and 42. The cup 44 includes an appropriate first matching flange 56 for matching with the mounting flange 32. The mounting flange 32 and the first matching flange 56 have aligned holes for receiving the nut and bolt combinations 40 and 42.

An annular space 66 between the cylinder 14 and the bore 26 is filled with the fluid 12 to be tested by first filling the cup 44 with the fluid 12, attaching the cup 44 to the tube 24 as illustrated, and then moving the tube 24 and cup 44 relatively axially toward the cylinder 14 sufficiently to force the fluid 12 go a desired height within the annulus 66, generally until the entire annulus 66 is filled. Thereafter, the cup 44 is removed after appropriate release of nut-bolt combinations 40, and 42 and a test closure 68, seen in FIG. 2, may be attached in place of the cup 44. The fluid 12 remains in the annulus 66 due to its viscosity and to the small dimensions of the annulus 66. The test closure 68 then forms a part of the axial fastening means 38 as will shortly be explained.

FIG. 2 shows the test closure 68 attached to the tube 24. The test closure 68 has a first end region 70 and a second end region 72, an interior cavity 74 which is generally cylindrical and which in any event is larger than the bore 26, and which extends from the first end region 70 toward the second end region 72. The first end region 70 of the closure 68 is detachably attachable to the second open end 30 of the tube 24 with the cavity 74 being generally coaxial with the bore 26. The closure 68 includes at least one pressure release hole 76 therethrough to eliminate any errors due to possible pressure buildup in cavity 74. The first end region 70 of the closure 68 is detachably attachable to the second open end 30 of the tube 24 via appropriate holes in a second matching flange 82, which holes are aligned with the holes in the mounting flange 32. The nut and bolt combinations 40 and 42 are used as with the loading cup 44. The second end region 72 has a bore 83 into which a rod end 85 of the hydraulic motor 36 fastens. The rod end 85 of the hydraulic motor 36 can also be attached to a bore 87 in the second end region 48 of the cup 44 to provide controlled axial movement of the cup 44 so that the annulus 66 can be controllably filled. Thus, the hydraulic motor 34 moves the tube 24 via the cup 44 or via the test closure 68, either of which forms a portion of the fastening means 38.

Measuring means 84 (FIG. 3) also form a part of the invention. The measuring means 84 serve for measuring the instantaneous force exerted on the cylinder 14 as the tube 24 moves axially. The preferred measuring means 84 comprises a load cell 86 axially attached to the first end 18 of the cylinder 14, generally via the threaded portion 22. A commercially available unit for serving as the measuring means 84 is a Materials Test System Corporation tensile or rotational testing apparatus normally used for testing mechanical properties of solids. Instron Company manufactures competitive apparatus which can also serve as the measuring means 84.

Referring principally to FIG. 3, a block diagram is shown of the system which illustrates the interrelationships and functions of the various components. The rheometer 10 is attached to the hydraulic actuator 36 from below and to the load cell from above (at the first end 18). A function generator 88 is such as to provide ramp, sine, square and saw-tooth signals. If desired, a programmable function generator can be used in place of or in addition to the function generator 88 thereby allowing for an infinite number of predesigned deformation histories to be imposed on the test fluid 12 in the annulus 66. The function generator 88 directs the fluid displacements by means of an input signal through the hydraulic actuator 36. The resulting vertical displacement of the driving rod or piston 85 of hydraulic actuator 36 is measured with a linear variable differential transformer 90, and the signal is fed to a servo-controller 92. The output from the load cell 86 can also be fed to the servo-controller as shown by a dashed line. Either the stress or the strain of the sample can be controlled independently. Stress and strain outputs can be monitored on an oscilloscope 94, a strip-chart recorder 96, or an X-Y recorder 98.

A particularly useful apparatus has been formulated wherein the cylinder 14 is about 43 centimeters long and 3.8 to 4 centimeters in diameter, and the tube 24 is about 25 centimeters long and slightly over 4 centimeters in diameter. The resultant very small and uniform annulus 66 leads to the obtaining of very accurate stress-strain measurements.

INDUSTRIAL APPLICABILITY

The present invention relates to a rheometer 10 useful for measuring the viscosity of fluids. The measurements are extremely accurate and are substantially free from edge effects. The rheometer 10 is particularly inexpensive to manufacture and is very easily loaded.

While the invention has been described in connection with specific embodiments thereof, it will be understood that it is capable of further modifications, uses or adaptations of the invention following, in general, the principles of the invention and including such departures from the present disclosure as come within known or customary practice in the art to which the invention pertains and as may be applied to the essential features hereinbefore set forth, and as fall within the scope of the invention and of the appended claims.

I claim:

1. A rheometer (10) comprising:
    a central cylinder (14) having an axis (16), a first end (18) and a second end (20);
    a tube (24) having a cylindrical bore (26), said bore (26) being slightly larger than said cylinder (14) and being positioned thereabout and coaxial therewith, said tube (24) having a first open end (28) and a second open end (30) aligned toward, respectively, said first end (18) and said second end (20) of said cylinder (14);
    a loading cup (44) having a first end portion (46), a second end portion (48), an interior cylindrical opening (50) larger than said bore (26) and extending from said first end portion (46) toward said second end portion (48), said first end portion (46) of said cup (44) being detachably attachable to said second open end (30) of said tube (24) with said cylindrical opening (50) generally coaxial with said bore (26);
    axial moving means (34) for controllably axially moving said tube (24) relative to said cylinder (14); and
    measuring means (84) for measuring instantaneous force exerted on said cylinder (14) as said tube (24) moves axially.

2. A rheometer (10) as set forth in claim 1, wherein said axial moving means (34) includes a test closure (68) having a first end region (70), a second end region (72), an interior cylindrical cavity (74) larger than said bore (26) and extending from said first end region (70) toward said second end region (72), said first end region (70) of said closure (68) being detachably attachable to said second open end (30) of said tube (24) with said cylindrical cavity (74) generally coaxial with said bore (26) when said first end portion (46) of said cup (44) is detached from said second open end (30) of said tube (24), said closure (68) including a pressure relief hole (76) therethrough.

3. A rheometer (10) as set forth in claim 2 wherein said second open end (30) of said tube (24) includes an outwardly extending mounting flange (32), said first end portion (46) of said cup (44) includes an outwardly extending first matching flange (56) adapted to be fastened to said mounting flange (32), and said first end region (70) of said closure (68) includes an outwardly extending second matching flange (82) adapted to be fastened to said mounting flange (32).

4. A rheometer (10) as set forth in claim 1, wherein said second open end (30) of said tube (24) includes an outwardly extending mounting flange (32), said first end portion (46) of said cup (44) includes an outwardly extending first matching flange (56) adapted to be fastened to said mounting flange (32).

5. A rheometer (10) as set forth in claim 1, wherein said axial moving means (34) comprise a hydraulic motor (36) and fastening means (38) for connecting the hydraulic motor (34) to drive the tube (24).

6. A rheometer (10) as set forth in claim 1, wherein said measuring means (84) comprise a load cell (86) in force conducting relation to said first end (18) of said cylinder (14).

* * * * *